United States Patent
Machaty et al.

(10) Patent No.: US 6,211,429 B1
(45) Date of Patent: Apr. 3, 2001

(54) COMPLETE OOCYTE ACTIVATION USING AN OOCYTE-MODIFYING AGENT AND A REDUCING AGENT

(75) Inventors: Zoltan Machaty, Columbia; Randall S. Prather, Rocheport, both of MO (US)

(73) Assignee: The Curators of the University of Missouri, Columbia, MO (US)

(*) Notice: Subject to any disclaimer, the term of this patent is extended or adjusted under 35 U.S.C. 154(b) by 0 days.

(21) Appl. No.: 09/100,167

(22) Filed: Jun. 18, 1998

Related U.S. Application Data (60) Provisional application No. 60/050,046, filed on Jun. 18, 1997.

(51) Int. Cl.$^7$ ............................. C12N 15/00; C12N 5/00

(52) U.S. Cl. ........................... 800/24; 435/325; 435/375

(58) Field of Search ................................. 435/325, 375; 800/24

(56) References Cited

PUBLICATIONS

Minamihashi et al (1993) Theriogenology 40, 63–76.*
Cheong et al (1993) Biology of Reproduction 48, 958–963.*
Piko et al (1982) Develop. Biol. 89, 662–678.*
Wolf et al (1998) J. Biotech. 65, 99–110.*
Fulka et al (1998) BioEssays 20, 847–851.*
Kono (1997) Rev. Reproduc. 2, 74–80.*
Bootman, Martin D., et al., "The Thiol Reagent, Thimerosal, Evokes $Ca^{2+}$ Spikes in HeLa Cells by Sensitizing the Inositol 1,4,5–Trisphosphate Receptor," The Journal of Biological Chemistry, vol. 267, No. 35, pp. 25113–25119, (Dec. 15, 1992).
Cheek, Timothy, R., et al., "Fertilisation and thimerosal stimulate similar calcium spiking patterns in mouse oocytes but by separate mechanisms," Development 119, pp. 179–189 (1993).
Kuriyama, Ryoko, et al., "Role of Tubulin—SH Groups in Polymerization to Microtubules," J. Biochem., vol. 76, No. 3, pp. 651–654 (1974).
Machaty, Zoltan, et al., "Complete Activation of Porcine Oocytes Induced by the Sulfhydryl Reagent, Thimerosal," Biology of Reproduction 57, pp. 1123–1127 (1997).
Swann, Karl, "Thimerosal causes calcium oscillations and sensitizes calcium–induced calcium release in unfertilized hamster eggs," Federation of European Biochemical Societies, vol. 278, No. 2, pp. 175–178 (Jan. 1991).
Swann, Karl, "Different triggers for calcium oscillations in mouse eggs involve a ryanodine–sensitive calcium store," Biochem. J., 287, pp. 79–84 1992).

Tanaka, Yuji, et al., "Thimerosal Potentiates $Ca^{2+}$ Release Mediated by Both the Inositol 1,4,5–Triphosphate and the Ryanodine Receptors in Sea Urchin Eggs," The Journal of Biological Chemistry, vol. 269, No. 15, pp. 11247–11253 (Apr. 15, 1994).

Tarin, Juan J., et al., "The oxidizing agent tertiary butyl hydroperoxide induces disturbances in spindle organization, c–meiosis, and aneuploidy in mouse oocytes," Molecular Human Reproduction, vol. 2, No. 12, pp. 895–901 (1996).

Yao, Jian–An, et al., "Mechanism of enhancement of slow delayed rectifier current by extracellular sulfhydryl modification," Am. J. Physiol. 273 (Heart Circ. Physiol. 42), pp. H208–H219 (1997).

Abramson, Jonathan J., et al., "Critical Sulfhydryls Regulate Calcium Release from Sarcoplasmic Reticulum," *Journal of Bioenergetics and Biomembranes*, vol. 21, No. 2, pp. 283–294, 1989.

Machaty, Z., et al., "Thimerosal induces full activation of pig oocytes," *Biology of Reproduction*, vol. 56, No. Suppl. 1, Abstract 603, p. 233, Aug. 1997.

Machaty, Z., et al., "Characteristics Of Thimerosal–Induced Activation of Pig Oocytes," *Theriogenology*, vol. 49, No. 1, p. 156, Jan. 1998.

Miyazaki, Shun–ichi, et al., "Antibody to the inositol triphosphate receptor blocks thimerosal–enhanced $Ca^{2+}$–induced $Ca^{2+}$ released and $Ca^{2+}$ oscillations in hamster eggs," *Federation of European Biochemical Societies*, vol. 309, No. 2, pp. 180–184, Sep. 1992.

\* cited by examiner

*Primary Examiner*—Deborah Crouch
(74) *Attorney, Agent, or Firm*—Senniger, Powers, Leavitt & Roedel (57) ABSTRACT

Provided is a method of parthenogenetically activating an unfertilized mammalian oocyte, comprising contacting an unfertilized mammalian oocyte with an oocyte-modifying agent followed by a reducing agent, wherein the mammalian oocyte is in contact with the oocyte-modifying agent and reducing agent, respectively, for a time and under conditions such that the unfertilized mammalian oocyte is activated. Also provided are methods for transplanting a nucleus from a cultured mammalian cell, mammalian embryo, mammalian fetus, or an adult mammal to a recipient mammalian oocyte; producing a cloned mammalian embryo; and producing a cloned mammal, as well as the cloned products produced by these methods. Finally, a method of studying genetic imprinting in mammals is also provided.

21 Claims, 2 Drawing Sheets

COMPLETE OOCYTE ACTIVATION USING AN OOCYTE-MODIFYING AGENT AND A REDUCING AGENT

This application claims the benefit of priority of U.S. Provisional Application Serial No. 60/050,046, filed Jun. 18, 1997.

BACKGROUND OF THE INVENTION

1. Field of the Invention

The present invention relates to the fields of animal husbandry and biomedicine. More particularly, the present invention relates to methods for improving the cloning of mammals.

2. Description of Related Art

Induction of Calcium Transients in Oocytes

Sperm-oocyte interaction triggers an increase in the intracellular free $Ca^{2+}$ concentration ($[Ca^{2+}]_i$) in oocytes, which in mammals takes the form of a series of repetitive $Ca^{2+}$ transients [1]. These transients are thought to be responsible for inducing cortical granule exocytosis to prevent polyspermy, and for oocyte activation and subsequent development.

Repetitive $Ca^{2+}$ transients can also be induced artificially using various agents [2]. Among them is thimerosal (sodium ethylmercurithiosalicylate), a sulfhydryl reagent that causes $Ca^{2+}$ release in a number of cell types by modifying sulfhydryl (—SH) groups on intracellular $Ca^{2+}$ release proteins. Thimerosal has been shown to induce repetitive $Ca^{2+}$ transients in hamster [3, 4], mouse [2, 5, 6], rabbit [7], bovine [8], and human [9, 10] oocytes.

Exposure of mouse oocytes to concentrations of thimerosal adequate to stimulate a train of $Ca^{2+}$ spikes (10, 50, and 100 $\mu$M) for 5 or 30 min induced zona pellucida hardening; 39 out of 40 (98%) mouse oocytes exposed to 100 $\mu$M thimerosal for 5 min followed by a 10 to 30 min wash showed cortical granule exocytosis [5]. Although thimerosal induced cortical granule release in this system, it did not activate oocytes: no polar body extrusion was observed in either control oocytes or oocytes treated with 20–100 $\mu$M thimerosal for 30 min followed by a two hour recovery period. Furthermore, the spindle was completely destroyed in 46 out of 50 (92%) oocytes exposed to 100 $\mu$M thimerosal for 11 to 40 min, and was severely disrupted in the remaining four oocytes. Thus, treatment of oocytes with thimerosal alone under these conditions does not lead to complete activation.

An earlier study carried out on purified porcine brain tubulin indicated that the oxidation of tubulin sulfhydryl groups by 5,5'-dithio-bis(2-nitrobenzoic acid) interferes with tubulin polymerization [11]. The same study also showed that the oxidation of tubulin sulfhydryl groups could be reversed by the sulfhydryl reducing agent dithiothreitol (DTT). In the mouse system [5], 73% (30 out of 41) of mouse oocytes exposed to 100 $\mu$M thimerosal for 5 min, then 20 $\mu$M thimerosal for 20 min, followed by a wash in thimerosal-free medium containing DTT for 15 min, regenerated typical metaphase spindles. Of the remaining 11 oocytes, 10 had slightly abnormal spindles, and one lacked a spindle.

Nuclear Transfer to Oocytes

Nuclear transfer is a procedure involving the replacement of the nucleus of one cell with that of another, permitting the creation of genetically identical individuals. Recent reports on the cloning of sheep and cattle through nuclear transfer, such as the birth of "Dolly" the cloned lamb (Wilmut et al. (1997) *Nature* 385:810–813), have focussed much attention on this aspect of reproductive biology. Despite the ability to clone sheep and cattle using nuclear transfer, a need exists for methods that will improve the probability of success of developing mammalian oocytes to produce embryos, fetuses, and eventually, infant and adult animals for agricultural, biomedical, and basic research purposes.

One means of cloning by nuclear transfer involves first treating an unfertilized egg with cytoskeletal inhibitors to depolymerize the microtubules and/or microfilaments, thereby imparting elasticity to the plasma membrane. The egg is then held in place with a fire-polished holding pipette, and another beveled micropipette is inserted through the zona pellucida (the protective layer surrounding the egg) of the oocyte and thrust into the cytoplasm. Since the plasma membrane is very elastic, it invaginates around the pipette. The chromosomes are located, either directly or after treatment with a DNA-specific dye and ultraviolet light illumination, and aspirated into the pipette. the pipette is then withdrawn, and the zona pellucida pinches off the cell membrane. This results in a membrane-bound nucleoplast in the pipette, and an oocyte containing no nucleus or chromosomes. A nuclear donor is then placed within the zona pellucida next to the recipient oocyte using a micropipette. The two cells are then induced to fuse using viral, chemical, or electrical stimuli to induce the fusion process. This results in deposition of the nucleus into the cytoplasm of the recipient oocyte, and a mixing of the cytoplasmic contents of the two cells. Many technical variations of this process can be employed without loss of subsequent development (reviewed by R. Prather (1996) *Proc. Soc. Exp. Biol. Med.* 212:38–43).

Next, there is a reconfiguration of the structure of the nucleus accomplished by a two-way exchange of proteins between the cytoplasm of the recipient oocyte and the chromatin of the donor nucleus. RNA synthesis is altered, the process being described as "nuclear reprogramming." If the nucleus is truly reprogrammed, it will reinitiate its developmental pathway and recapitulate early developmental events of the embryo (Prather et al. (1991) In *Animal Applications of Research in Mammalian Development*, R. A. Pedersen et al., Eds., The Cold Spring Harbor Laboratory Press, pp. 205–232).

Thirdly, another event that must occur for subsequent development of the nuclear transfer embryo is activation of the oocyte. The mammalian oocyte is generally arrested at metaphase-II of meiosis. Fertilization through the sperm-oocyte interaction triggers an increase in the intracellular free $Ca^{2+}$ concentration ($[Ca^{2+}]_i$) in the oocyte, which, as noted above, takes the form of a series of repetitive $Ca^{2+}$ transients in mammals [1]. These $Ca^{2+}$ transients are thought to be responsible for inducing exocytosis of specialized secretory vesicles, described as cortical granules, which are located under the plasma membrane of the egg cytoplasm granules. The contents of the granules are thought to be responsible fo the prevention of polyspermy and for breaking the arrest of meiosis, thereby activating development of the oocyte. Additionally, other features associated with the activation of oocytes include polar body extrusion, hardening of the zona pellucida, and regeneration of the metaphase spindles, which leads to the ability of the oocyte to support subsequent development.

When performing nuclear transfer, it is necessary to artificially break this meiotic arrest, otherwise the nuclear transfer recipient will remain arrested at the 1-cell stage with condensed chromosomes. Artificial methods of activating oocytes include the electrical pulse used for fusion of the donor cell, or chemical activation.

Many methods of oocyte activation have been described for the pig. However, many procedures that work well in other species do not work well in the pig. Furthermore, many previous activation protocols only work in vivo, which involves considerable expense to perform. Thus, there is a need for methods that result in in vitro development to the blastocyst stage in porcine oocytes.

SUMMARY OF THE INVENTION

The present invention meets the foregoing need in the art by providing methods enabling either in vitro or in vivo development of activated oocytes.

As discussed above, previous studies have shown that oxidation of tubulin sulfhydryl groups can be reversed by DTT, and metaphase spindles destroyed by oocyte exposure to thimerosal can also be regenerated by exposure to DTT. No other effects of thimerosal/DTT treatment have been reported. While other workers have attempted to use thimerosal to induce activation, no observations other than a series of calcium transients, zona hardening, and cortical granule exocytosis have been reported. In mouse oocytes, pronuclear formation or other evidence of activation following multiple transients was not observed [5].

Surprisingly, the present inventors have discovered that the combined use of an —SH or oocyte-modifying agent such as thimerosal and an —SH or thiol group reducing agent such as dithiothreitol is able to induce complete activation of mammalian oocytes. Coupling of a short treatment with thimerosal permitting only a single calcium transient before treatment with a reducing agent such as DTT to achieve activation is particularly effective. Thimerosal triggers a train of $Ca^{2+}$ spikes in mammalian oocytes. If followed by an incubation with a reducing agent such as DTT, such treatment can stimulate pronuclear formation. The combined thimerosal/DTT treatment also induces cortical granule exocytosis, subsequent hardening of the zona pellucida, and development of the activated oocytes to the blastocyst stage.

Accordingly, in one aspect, the present invention provides a method of activating an unfertilized mammalian oocyte, comprising contacting the unfertilized mammalian oocyte with an oocyte-modifying agent followed by a reducing agent, wherein the mammalian oocyte is in contact with an effective amount of each of the oocyte-modifying agent and the reducing agent, respectively, for a time and under conditions such that the unfertilized mammalian oocyte is activated. In a particular embodiment, the method comprises contacting an unfertilized mammalian oocyte with thimerosal for about 10 minutes, followed by contacting the unfertilized mammalian oocyte with dithiothreitol for about 30 minutes. A culture period or wash, designed to eliminate any remaining oocyte-modifying agent/reducing reagent, can follow. The oocyte can then be cultured in vivo or in vitro to at least the pronuclear stage, i.e, to the pronuclear stage or beyond, for example to the 2-cell stage, 4-cell stage, the blastocyst stage, or anywhere in between.

In another aspect, the present invention provides a method for transplanting a nucleus from a mammalian cell, which can be a cultured mammalian cell, to a recipient mammalian oocyte, comprising:

(a) isolating the membrane-bounded nucleus from a mammalian cell;

(b) removing the nuclear chromosomal material from a recipient mammalian oocyte, thereby preparing an enucleated recipient mammalian oocyte;

(c) introducing the membrane-bounded nucleus from the mammalian cell into the enucleated recipient mammalian oocyte to form an oocyte containing the nucleus from the mammalian cell;

(d) reprogramming the developmental cascade of events of the nucleus from the mammalian cell;

(e) contacting the oocyte containing the nucleus from the mammalian cell of step (d) with an effective amount of each of an oocyte-modifying agent followed by a reducing agent, wherein the oocyte is in contact with the oocyte-modifying agent and reducing agent, respectively, for a time and under conditions such that the oocyte is activated; and (f) culturing the activated oocyte of step (e) in vitro or in vivo.

Introduction of the membrane-bounded nucleus of the mammalian cell into the enucleated recipient mammalian oocyte in step (c) of this and the other methods disclosed hereinbelow can be achieved by fusing together the membrane of the membrane-bounded nucleus from the mammalian cell with the membrane of the enucleated recipient mammalian oocyte. Alternatively, this can be achieved by introducing the membrane-bounded nucleus from the mammalian cell into the enucleated recipient mammalian oocyte by microinjection to form an oocyte containing the nucleus from the mammalian cell. Other methods for achieving the same results are described below.

Functionally, the oocyte-modifying and reducing agents contemplated for use in the present invention include those that, when used in combination with one another according to the methods disclosed herein, are effective in inducing activation of mammalian oocytes.

In another aspect, the present invention provides a method for transplanting a nucleus from a mammalian embryo to a recipient mammalian oocyte, comprising:

(a) isolating the membrane-bounded nucleus from a cell of a mammalian embryo;

(b) removing the nuclear chromosomal material from a recipient mammalian oocyte, thereby preparing an enucleated recipient mammalian oocyte;

(c) introducing the membrane-bounded nucleus from the cell of the mammalian embryo into the enucleated recipient mammalian oocyte to form an oocyte containing the nucleus from the cell of the mammalian embryo;

(d) reprogramming the developmental cascade of events of the nucleus from the cell of the mammalian embryo;

(e) contacting the oocyte containing the nucleus from the cell of the mammalian embryo of step (d) with an effective amount of each of an oocyte-modifying agent followed by a reducing agent, wherein the oocyte is in contact with the oocyte-modifying agent and the reducing agent, respectively, for a time and under conditions such that the oocyte is activated; and (f) culturing the activated oocyte of step (e) in vitro or in vivo.

In a further aspect, the present invention provides a method for transplanting a nucleus from a mammalian fetus to a recipient mammalian oocyte, comprising:

(a) isolating the membrane-bounded nucleus from a cell of a mammalian fetus;

(b) removing the nuclear chromosomal material from a recipient mammalian oocyte, thereby preparing an enucleated recipient mammalian oocyte;

(c) introducing the membrane-bounded nucleus from the cell of the mammalian fetus into the enucleated recipient mammalian oocyte to form an oocyte containing the nucleus from the cell of the mammalian fetus;

(d) reprogramming the developmental cascade of events of the nucleus from the cell of the mammalian fetus;

(e) contacting the oocyte containing the nucleus from the cell of the mammalian fetus of step (d) with an effective amount of each of an oocyte-modifying agent followed by a reducing agent, wherein the oocyte is in contact with the oocyte-modifying agent and the reducing agent, respectively, for a time and under conditions such that the oocyte is activated; and (f) culturing the activated oocyte of step (e) in vitro or in vivo.

In yet a further aspect, the present invention provides a method for transplanting a nucleus from an adult mammal to a recipient mammalian oocyte, comprising:

(a) isolating the membrane-bounded nucleus from a cell of an adult mammal;

(b) removing the nuclear chromosomal material from a recipient mammalian oocyte, thereby preparing an enucleated recipient mammalian oocyte;

(c) introducing the membrane-bounded nucleus from the cell of the adult mammal into the enucleated recipient mammalian oocyte to form an oocyte containing the nucleus from the cell of the adult mammal;

(d) reprogramming the developmental cascade of events of the nucleus from the cell of the adult mammal;

(e) contacting the oocyte containing the nucleus from the cell of the adult mammal of step (d) with an effective amount of each of an oocyte-modifying agent followed by a reducing agent, wherein the oocyte is in contact with the oocyte-modifying agent and the reducing agent, respectively, for a time and under conditions such that the oocyte is activated; and (f) culturing the activated oocyte of step (e) in vitro or in vivo.

In yet another aspect, the present invention provides a method for producing a cloned mammalian embryo, comprising:

(a) isolating a membrane-bounded nucleus from a cell of a mammalian embryo;

(b) removing the nuclear chromosomal material from a recipient mammalian oocyte, thereby preparing an enucleated recipient mammalian oocyte;

(c) introducing the membrane-bounded nucleus from the cell of the mammalian embryo into the enucleated recipient mammalian oocyte to form an oocyte containing the nucleus from the cell of the mammalian embryo;

(d) reprogramming the developmental cascade of events of the nucleus from the cell of the mammalian embryo;

(e) contacting the oocyte containing within its cytoplasm the nucleus from the cell of the mammalian embryo of step (d) with an effective amount of each of an oocyte-modifying agent followed by a reducing agent, wherein the oocyte is in contact with the oocyte-modifying agent and the reducing agent, respectively, for a time and under conditions such that the oocyte is activated; and (f) culturing the activated oocyte of step (e) in vivo or in vitro to produce a cloned mammalian embryo.

In still a further aspect, the present invention provides a method for producing a cloned mammal, comprising:

(a) isolating a membrane-bounded nucleus from a cell of a mammal;

(b) removing the nuclear chromosomal material from an unfertilized recipient mammalian oocyte, thereby preparing an enucleated recipient mammalian oocyte;

(c) introducing the membrane-bounded nucleus from the cell of the mammal into the enucleated recipient mammalian oocyte to form an oocyte containing the nucleus from the cell of the mammal;

(d) reprogramming the developmental cascade of events of the nucleus from the cell of the mammal;

(e) contacting the oocyte containing within its cytoplasm the nucleus of the cell from the mammal with an effective amount of each of an oocyte-modifying agent followed by a reducing agent, wherein the oocyte is in contact with the oocyte-modifying agent and the reducing agent, respectively, for a time and under conditions such that the oocyte is activated;

(f) culturing the activated oocyte of step (e) in vitro or in vivo; and (g) transferring the cultured, activated oocyte of step (f) to the oviduct or uterus of a recipient maternal mammal to produce a cloned mammal.

In step (a) of the foregoing method, a preferred cell is one from a mammary gland, preferably from a mammal of the same species as that of the unfertilized recipient mammalian oocyte.

If microinjection is employed in step (c) of any of the foregoing methods, it is not necessary that the nucleus from the donor cell be present within the donor cell plasma membrane.

In yet a further aspect, the present invention provides a method of studying genetic imprinting in a mammal, comprising:

(a) contacting an unfertilized mammalian oocyte with an effective amount of each of an oocyte-modifying agent followed by a reducing agent, wherein the unfertilized mammalian oocyte is in contact with the oocyte-modifying agent and the reducing agent, respectively, for a time and under conditions such that the unfertilized mammalian oocyte is activated; and (b) determining whether a gene of interest is expressed or not during culturing of the activated mammalian oocyte.

Genetic imprinting can be studied in any of the activated mammalian oocytes produced in accordance with any of the methods described hereinabove or elsewhere herein.

In any of the foregoing methods, the oocyte-modifying agent-treated oocyte can subsequently be contacted with the reducing agent in any of several different ways. For example, the oocyte-modifying agent-treated oocyte can be transferred from the medium containing the oocyte-modifying agent, and placed directly into medium containing the reducing agent without any intermediate wash step. Alternatively, the reducing agent can be added directly to the oocyte-modifying agent-treated oocyte in the presence of the oocyte-modifying agent. As another alternative, the oocyte-modifying agent agent can be removed, for example by washing the oocyte with control medium or medium containing the reducing agent, prior to incubation of the oocyte in medium containing the reducing agent. In any event, the manner of contacting the oocyte-modifying agent-treated oocyte with the reducing agent is not critical.

In any of the foregoing methods, culturing of the activated oocyte can be carried out for a time and under conditions sufficient to wash out or substantially eliminate the oocyte-modifying agent and/or reducing agent. Thereafter, the activated oocyte can be transferred to an oviduct, or alternatively, cultured for up to about one week and then transferred to the uterus of a surrogate animal.

Finally, the present invention encompasses the living, cloned products produced by each of the methods described herein.

Further scope of the applicability of the present invention will become apparent from the detailed description and drawings provided below. However, it should be understood that the following detailed description and examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed description taken in conjunction with the accompanying drawings, all of which are given by way of illustration only, and are not limitative of the present invention, in which:

FIGS. 1A–1C show changes in the $[Ca^{2+}]_i$ of porcine oocytes induced by thimerosal. FIG. 1A: Arrow indicates the addition of thimerosal to the oocytes at a final concentration of 200 µM; this typically triggered a series of $Ca^{2+}$ transients. FIG. 1B: The thimerosal (first arrow)-induced $Ca^{2+}$ transients are totally blocked by DTT (second arrow) at a final concentration of 8 mM.

DETAILED DESCRIPTION OF THE INVENTION

The following detailed description is provided to aid those skilled in the art in practicing the present invention. Even so, this detailed description should not be construed to unduly limit the present invention as modifications and variations in the the embodiments discussed herein can be made by those of ordinary skill in the art without departing from the spirit or scope of the present inventive discovery.

The contents of each of the references cited herein, including those of the references cited within these primary references, are herein incorporated by reference in their entirety.

The present invention provides a method for activating unfertilized mammalian oocytes by sequentially exposing such oocytes to an oocyte-modifying agent followed by a reducing agent. Such unfertilized mammalian oocytes are often, but not always, arrested at meiotic metaphase, and can include oocytes arrested at the germinal vesicle stage, meiotic metaphase I, meiotic metaphase II, or the pronuclear stage.

As used herein, the term "activation" refers to the capacity of an unfertilized oocyte to develop to at least the pronuclear stage, or beyond, after treatment with an oocyte-modifying agent and a reducing agent. Generally speaking, the pronuclear stage is achieved about three to seven hours after such treatment. Oocytes activated by the methods disclosed herein can undergo partial parthenogenetic development to the 2-cell stage, the blastocyst stage, or anywhere in between upon culturing in vitro or in vivo.

The term "oocyte-modifying agent" refers to an agent that can react with a substrate on or in an oocyte, for example a thiol (—SH) group, which can be a protein thiol group; the effect of this reaction, when followed by treatment of the oocyte with a reducing agent according to the methods disclosed herein, results in activation of mammalian oocytes. Non-limiting examples of oocyte-modifying agents useful in the present invention include oxidizing agents, alkylating agents, etc. Thimerosal is thought to modify protein thiol groups as follows: Thimerosal+protein-SH→protein—S—S—Hg—$CH_2$–$CH_3$ (Yao et al. (1997) *Am. J. Physiol.* 273 (*Heart Circ. Physiol.* 42):H208–H219).

Oocyte-modifying agents believed to be useful in the present invention include, but are not limited to, thimerosal; t-butyl hydroperoxide; thiourea;

phenylephrine; N-aklylmaleimides such as N-ethylmaleimide; oxidized glutathione; α-haloacids such as iodoacetate, chloroacetate, and bromoacetate; iodoacetamide; p-mercuribenzoate; p-chloromercuribenzoate; 5,5'-dithiobis(2-nitrobenzoic acid) (DTNB); (2-trimethylammonium)ethylmethanethiosulfonate (MTSET); and (2-sulfonatoethyl)methanethiosulfonate (MTSES). Useful reducing agents, such as thiol (—SH) group reducing agents, are believed to include DTT; dithioerythritol (DTE); β-mercaptoethanol; cysteine; reduced glutathione; reduced thiourea; thioglycolate; and ascorbic acid. Other oocyte-modifying and reducing agents useful in the present invention can be readily identified by determining their effectiveness through screening using routine methods such as those described in Examples 1–5, below. Furthermore, it should be understood that two or more oocyte-modifying agents can be used in combination with one another; similarly, two or more reducing agents can be used together in combination.

The concentration of the oocyte-modifying agent can be in the range of from about 1 nM to about 1 mM, preferably from about 100 nM to about 750 µM, more preferably from about 1 µM to about 500 µM, still more preferably from about 20 µM to about 250 µM, even more preferably from about 50 µM to about 200 µM, and most preferably from about 100 µM to about 200 µM. In the experiments described herein, the oocyte-modifying agent was thimerosal, employed at a final concentration of 200 µM.

The concentration of the reducing agent can be in the range of from about 0.1 mM to about 250 mM, preferably from about 1 mM to about 100 mM, more preferably from about 2 mM to about 50 mM, still more preferably from about 3 mM to about 30 mM, even more preferably from about 4 mM to about 20 mM, and most preferably from about 5 mM to about 10 mM. In the experiments described herein, the reducing agent was DTT, employed at a final concentration of 8 mM.

The concentrations of other oocyte-modifying and reducing agents useful in the present invention can be readily determined by screening using routine methods such as those described in Examples 1–5, below.

The time period during which oocytes are contacted with the oocyte-modifying agent should be a period effective to result in activation thereof when followed by treatment with a reducing agent. Such time period can be in the range of from about 5 min to about 20 min, preferably from about 5 min to about 15 min, more preferably from about 5 min to about 12 min. Depending upon the oocyte maturation system (in vivo vs. in vitro) and the medium used therefor, the medium in which the oocyte is exposed to the oocyte-modifying and reducing agent, and the medium used during measurement of calcium transients, the duration of exposure of the oocyte to the oocyte-modifying agent can be from about 10 to about 12 min.

The time period during which such eggs are contacted with the reducing agent should be a period effective to result in activation thereof when preceded by treatment with an oocyte-modifying agent. Such time period can be in the range of from about 5 minutes to about 1 hour, preferably from about 10 minutes to about 45 minutes, more preferably from about 20 minutes to about 40 minutes, and most preferably about 30 minutes.

Contacting of the unfertilized mammalian oocyte with the reducing agent following the oocyte-modifying agent can be substantially immediately, or can comprise a time interval in the range of from about 5 seconds to about 5 minutes after exposure of the oocyte to the oocyte-modifying agent. The oocyte-modifying agent-treated oocyte can be transferred into medium containing the reducing agent without any intermediate wash step. Alternatively, the oocyte-modifying agent-treated oocyte can be washed in control or reducing agent-containing medium to substantially remove oocyte-modifying agent before culturing in reducing agent-containing medium. As another alternative, the reducing agent can be added directly to the oocyte while the latter is still present in oocyte-modifying agent-containing medium.

The methods described herein are generally applicable to a wide array of unfertilized mammalian oocytes, including, but not limited to, unfertilized porcine oocytes, unfertilized bovine oocytes, unfertilized mouse oocytes, unfertilized sheep oocytes, unfertilized goat oocytes, unfertilized horse oocytes, unfertilized cat oocytes, unfertilized dog oocytes, and unfertilized human oocytes.

Generally speaking, the methods of activating unfertilized mammalian oocytes disclosed herein facilitate partial parthenogenetic development of such eggs so that development thereof can proceed to the 2-cell stage, to at least the blastocyst stage, or anywhere in between, upon culturing in vitro or in vivo. Phenomena which may be involved in initiating this developmental program can include any of the following: the production of $Ca^{2+}$ transients (Machaty et al. (1997) Biol. Reprod. 56:921–930); cortical granule release (Kim et al. (1996) J. Reprod. Fertil. 107:79–86); zona pellucida hardening; destruction of maturation-promoting factor, measured indirectly by determining histone H1 kinase activity (Machaty et al. (1996) Biol. Reprod. 54:316–322); pronuclear formation; ribosomal RNA/mRNA synthesis; and changes in protein profiles (Ding et al. (1992) Mol. Reprod. Dev. 31:287–296).

As those of ordinary skill in the art will readily appreciate, one important application of the present method of oocyte activation lies in the field of mammalian cloning by nuclear transfer. Thus, the present method can be employed in conjunction with conventional methods of mammalian cloning well known to those skilled in the art.

The procedures involved in nuclear transfer (reviewed by Gurdon (1977) Methods in Cell Biology, Vol. 16, pages 125–139, Academic Press, New York; Bondioli (1993) Mol. Reprod. Dev. 36:274–275; Clement-Sengewald & Brem (1992) Berl. Munch. Tierarztl. Wochenschr. 105:15–21; Prather (1996) Proc. Soc. Exp. Biol. & Med. 212:38–43) generally involve removing the genetic material from an unfertilized egg or oocyte, and then introducing therein a nucleus from a cell of an adult, fetus, embryo, or cell line. These basic procedures were first proposed by Spemann ((1938) Embryonic Development and Induction, pages 210–211, Hafner, N.Y.) and developed in amphibians (Briggs et al. (1952) Proc. Natl. Acad. Sci. USA 38:455–463). Many modifications have been introduced over the years, including the use of viruses to mediate cell fusion (Graham (1969) Wistar Inst. Symp. Monogr. 9:19–33; McGrath et al. (1983) Science 220:1300–1302); chemically induced cell fusion (Fisher et al. (1981) Tech. Cell. Physiol. 1:1–36); electrically induced cell fusion (Berg (1982) Bio-electrochem. Bioenerg. 9:223–228; Robl et al. (1987) J. Anim. Sci. 64:642–647); microinjection as in amphibians (Collas et al. (1994) Mol. Reprod. Dev. 38:264–267); and chemical treatment to relax the cytoskeleton, microtubules, and microfilaments (colchicine or colcemid, and cytochalasins, respectively, (McGrath et al. (1983) Science 220:1300–1302). A variety of different cells have been used, including those from early embryos (Prather et al. (1987) Biol. Reprod. 37:859–866; Prather et al. (1989) Biol. Reprod. 41:414–418); fetuses (Campbell et al. (1996) Nature 380:64–66); and fetal cell lines and adults (Wilmut et al. (1997) Nature 385:810–813). Activation has generally been induced with an electric pulse in the presence of calcium (Prather et al. (1987) Biol. Reprod. 37:859–866), or with compounds that interact with different parts of the pathway of the production of free intracellular calcium (reviewed by Prather et al. (1997) Korean J. Anim. Reprod. 20:395–412). However, this activation has also been achieved with a number of other chemical treatments that do not involve calcium, e.g., protein kinase inhibition (Mayes et al. (1995) Biol. Reprod. 53:270–275), or inhibition of protein synthesis (Nussbaum et al. (1995) Mol. Reprod. Dev. 41:70–75). The first patent relating to a mammalian cloning procedure was that of Prather et al., U.S. Pat. No. 4,994,384.

Introduction of a membrane-bound nucleus from a donor mammalian cell into an enucleated recipient mammalian oocyte to form an oocyte containing the donor nucleus can be performed by fusing together the membrane of the membrane-bound nucleus from the donor mammalian cell with the membrane of the enucleated recipient mammalian oocyte to form an oocyte containing the nucleus from the donor mammalian cell. Alternatively, such introduction can be performed by microinjecting the membrane-bounded nucleus from the mammalian donor cell into the enucleated recipient mammalian oocyte to form an oocyte containing the nucleus from the donor mammalian cell. As those of ordinary skill in the art are aware, further alternative means exist for introducing donor nuclear material into a recipient oocyte. For example, and not by way of limitation, one can introduce a donor cell (or nucleus) into the space under the zona pellucida or into the perivitelline space of the enucleated, recipient oocyte, and then subsequently carry out membrane fusion to produce an oocyte containing within its cytoplasm the donor nucleus.

All means of introducing donor nuclear material into an enucleated recipient mammalian oocyte known to those of ordinary skill in the art are useful in the methods disclosed herein.

The claims appended hereto recite contacting the recipient oocyte containing the nucleus from the donor mammalian cell within its cytoplasm with an oocyte-modifying agent followed by a reducing agent to activate the oocyte. Alternatively, this contacting/activating treatment can precede the step of introducing the donor nucleus into the unfertilized, recipient mammalian oocyte. Thus, the enucleated, unfertilized recipient mammalian oocyte can be subjected to the contacting/activating treatments as described herein, and the donor nucleus can then subsequently be introduced into the cytoplasm of the activated recipient mammalian oocyte.

With regard to the concept of "reprogramming the developmental cascade" of events of the nucleus of a donor cell, the inventors note that this involves a two-way exchange of protein between the cytoplasm of the unfertilized recipient oocyte and the chromatin of the donor nucleus, thus modifying the developmental status of the nucleus [28]. Such reprogramming would occur in connection with all the different types of nuclear transfers encompassed by the methods disclosed herein employing any type of donor cell, and cloned offspring would result regardless of cell type. In the case of an embryo cell line, one would expect the least amount of reprogramming to occur. A somewhat greater amount of reprogramming would occur with fetal cells, and an even greater amount would occur with cells from a cultured cell line. The greatest amount of reprogramming is expected to occur when using a differentiated cell line, for example a cell from an adult.

As those of ordinary skill will recognize, an important application of the present method involves the use of donor cells, for example those from a cell line, regardless of source, that have been transfected with a gene or other structural coding sequence of interest, for example one encoding a growth hormone, placental lactogen, etc., or containing a gene or other structural coding sequence that has been genetically modified prior to carrying out nuclear transfer. In this case, the product would be a transgenic animal with a modified characteristic.

One interesting, non-limiting example of such procedures involves development of transgenic pigs for xenotransplantation. Organ transplantation has become a very successful treatment for many diseases associated with terminal organ failure. The large scale success in transplantation of solid organs including heart, kidney, liver, and lung can be directly attributed to the introduction of the specific immunosuppressant Cyclosporin A (Weil (1984) *Medicinal Res. Rev.* 4:221–265). However, as a consequence of the success of organ transplantation, in terms of lives saved and quality of life for organ recipients, there has been an acute shortage in organ availability. In 1994, over 37,000 individuals were registered for transplantation, while only 18,000 transplants were performed in 1993 (Nasto et al. (1995) Lab. Animal 24:22–27). Since the supply of donor organ is almost exclusively dependent on the availability of cadaver organs, it has become clear that the number of available organs will never meet the demand. The need for other sources of donor organs has therefore become obvious. Among the potential xenograft organ donors, the most obvious ones appear to be non-human primates. However, for ethical reasons, as well as for reasons of supply, generation time, and potential issues related to infectious diseases, use of non-human primates as xenograft donors is not realistic.

In contrast to non-human primates, the pig offers many obvious advantages, including a generation time of less than one year and multiple offspring, as well as physiological properties of the organs that are similar to those of humans (D. H. Sachs (1992) in *Swine in Biomedical Research*, M. M. Swindle et al., Eds. Iowa State University Press, Ames, Iowa, p. 3); D. H. Sachs (1994) Vet. *Immuno. Immunopath.* 43:185–191). One considerable obstacle to evaluation of pig organs in the clinic is related to natural human antibody-mediated hyperacute rejection of pig tissues. In the discordant transplantation systems, such as pigs to humans, or pigs to non-human primates, detailed analysis has revealed that epitopes for natural antibodies include certain sugar moieties, specifically Gal $\alpha(1,3)$ Gal, whch is expressed ubiquitously on the surface of most cells (Sandrin et al. (1993) *Proc. Natl. Acad. Sci. USA* 90:11391–11395). Binding of human antibodies to this epitope results in a hyperacute destruction of the graft in a manner of minutes. Despite the problems related to hyperacute rejection, the pig is considered to be the species of choice to be developed for xenotransplantation by most pioneers in the field. One approach for overcoming this problem is to knock-out the $\alpha$-1,3-galactosyltransferase gene in pigs. Expression of this enzyme can be disrupted by homologous recombination using an inactive, mutant form of the encoding structural DNA. Mice in which the $\alpha$-1,3-galactosyltransferase gene has been knocked-out are viable and have normal organs, but develop cataracts (Tearle et al. (1996) *Transplantation* 61:13–19). Less xenoantibody from human serum binds to cells and tissues of these mice compared to those of normal mice, and there is also less activation of human complement on the cells from such mice. These results suggest that knockout of the $\alpha$-1,3-galactosyltransferase gene in pigs would be a useful means of overcoming the problem of hyperacute rejection. In addition, a number of genes involved in cardiovascular health and lipoprotein metabolism which could be modified to provide research models in animals are applicable to the treatment of human diseases.

Transfection methods are well known in the art as disclosed, for example, by Ausubel et al. (1989) *Current Protocols in Molecular Biology*, John Wiley & Sons, Inc., and Sambrook et al. (1989) *Molecular Cloning: A Laboratory Manual*, Second Edition, Cold Spring Harbor Laboratory Press, Cold Spring Harbor, N.Y.

"Genetic imprinting" refers to the phenomenon of differential genetic contribution by each parent to their offspring: gene expression in an embryo depends upon the sex of the parent from which a particular allele is inherited. Conventional molecular biological and other methods for studying gene expression associated with genetic imprinting are well known in the art, and are also described, for example, in Ausubel et al. and Sambrook et al., supra. Such methods include, for example, detection of mRNA synthesis, reverse transcriptase/PCR methods, screening of expresesion libraries, nucleic acid hybridization, immunological methods, electrophoretic methods, etc.

The following non-limiting examples illustrate the invention.

EXAMPLE 1

Activation of Porcine Oocytes by Thimerosal and Dithiothreitol

Materials and Methods

Chemical Reagents

Dithiothreitol (DTT) was purchased from Fisher Scientific (Pittsburgh, PA); fura-2 AM and pluronic F-127 were purchased from Molecular Probes, Inc. (Eugene, Oreg.). All other chemicals were obtained from Sigma Chemical Co. (St. Louis, Mo.).

Oocytes

Porcine oocytes were obtained from ovaries collected at a slaughterhouse. They were matured in NCSU-23 medium (Petters et al. (1993) *J. Reprod. Fertil. Suppl.* 48:61–73) containing 10% porcine follicular fluid, 10 IU/ml eCG (equine chorionic gonadotropin), 10 IU/ml hCG (human chorionic gonadotropin), 0.1 mg/ml cysteine, and 10 ng/ml epidermal growth factor (EGF) for 22h. This was followed by a culture in the same medium without hormonal supplementation for an additional 22 h [12]. Mature oocytes were freed of cumulus cells by vigorous pipetting in the presence of 0.3 mg/ml hyaluronidase, and the cellular responses to being incubated with 200 μM thimerosal were investigated.

Changes in the $[Ca^{2+}]_i$ were estimated using the $Ca^{2+}$ indicator dye fura-2. Oocytes were incubated in the presence of 2 μM of the acetoxymethyl ester (AM) form of the dye together with 0.02% pluronic F-127 in Hepes-buffered Tyrode's medium (HbT; [13]). After loading of the dye, thimerosal was added to the cells at a final concentration of 200 μM. Fluorescence recordings were performed using a Photoscan-2 photon counting fluorescence microscope system (Nikon Corp., Tokyo, Japan). Excitation wavelengths of 340 and 380 nm were alternated by a rotating chopper disk. The emitted fluorescence intensity was measured at 510 nm with a photomultiplier tube after background subtraction. $[Ca^{2+}]_i$ is presented as the ratio of fluorescence at 510 nm excited by the alternate UV excitation at 340 nm and 380 nm. Ratios of 1.2 and 6.5 correspond to 65 nM and 602 nM $Ca^{2+}$, respectively [14].

Porcine oocytes were exposed to 200 μM thimerosal for 10 or 30 min with or without transfer to and subsequent incubation in 8 mM DTT for 30 min, and then cultured in HbT medium. Six hours after the beginning of the thimerosal treatment, the oocytes were fixed in 25% (v:v) acetic alcohol for 48 h. Fixed oocytes were stained with 1% (w:v) aceto-orcein and evaluated for chromatin configuration. The treatment that was most effective in stimulating pronuclear formation was tested further.

The assessments of the cortical granules in the activated oocytes were performed as described earlier [15], with some modifications [16]. Oocytes were treated with 200 μM thimerosal (made up in HbT) for 10 min, followed by a 30 min incubation in HbT in the presence of 8 mM DTT. Two hours after the beginning of the thimerosal incubation, the zonae pellucidae were removed using 0.1% pronase. After being washed 3 times with PBS (phosphate buffered saline), zona-free oocytes were fixed with 3.7% paraformaldehyde in PBS for 30 min, followed by washing thoroughly in PBS containing 3 mg/ml BSA and 100 mM glycine for 15 min. After being incubated in PBS containing 0.1% Triton X-100 for 5 min, the oocytes were rinsed 2 more times. They were then cultured in 100 μg/ml fluorescein isothiocyanate-labelled peanut agglutinin (FITC-PNA) in PBS for 30 min. After staining, the oocytes were washed in PBS containing 3 mg/ml BSA and 0.01% Triton X-100, mounted on slides, and examined with a laser scanning confocal microscope. Confocal microscopy was performed using a BioRad MRC-600 equipped with a krypton-argon ion laser and mounted on an Optiphoto II Nikon microscope. The number of cortical granules at the cortex was counted at a square of 100–1000 μm² (depending upon density), and the average number of cortical granules/100 μm² cortex in each oocyte was calculated.

Hardening of the zona pellucida was investigated by determining the time which was necessary to dissolve the zona in a 0.1% pronase solution. After the combined 10 min thimerosal/30 min DTT treatment, the oocytes were cultured in HbT for 2 h, then transferred into 500 μl of pronase solution made up in protein-free PBS, ten at a time. Zona removal was aided by gentle pipetting of the oocytes, and the time needed for total digestion of the zona pellucida in half of the oocytes was recorded.

To investigate the developmental potential of the thimerosal/DTT-treated oocytes, they were incubated for 6 days either in vitro or in vivo. For in vitro cultivation, NCSU-23 medium supplemented with 0.1 mg/ml cysteine and 4 mg/ml BSA was used. In vivo development was examined by transferring the activated oocytes into ligated porcine oviducts (Jolliff et al. (1997) Biol. Reprod. 56:544–548). At the end of the incubation period, the embryos were evaluated for the state of development. The number of inner cell mass (ICM) and trophectoderm (TE) nuclei in the blastocysts was determined using a differential staining method described previously [17]. Briefly, zona pellucidae were removed by a brief exposure to 0.1% pronase solution, and the zona-free embryos were exposed to a 1:5 dilution of rabbit anti-pig whole serum (Sigma P-3164; dialyzed in HbT without serum to remove sodium azide) for 40 min. After three rinses in HbT medium, the embryos were transferred into HbT containing a 1:10 dilution of guinea pig complement (Sigma S-1639), 2 μg/ml Hoechst 33342, and 10 μg/ml propidium iodide, for 40 min. The number of ICM and TE cells were counted under UV light using a Nikon Diaphot inverted microscope (Nikon Corp., Tokyo, Japan), fitted for epi-fluorescence.

Controls included non-treated oocytes or oocytes exposed to DTT only. Rates of pronuclear and compact morula/blastocyst formation were compared by chi-square analysis. The difference between the mean times required to digest the zona pellucida of oocytes in different experimental groups was determined by calculating protected least-significant differences using Multivariate General Linear Hypothesis of Systat [18].

Results

Figure 1A:
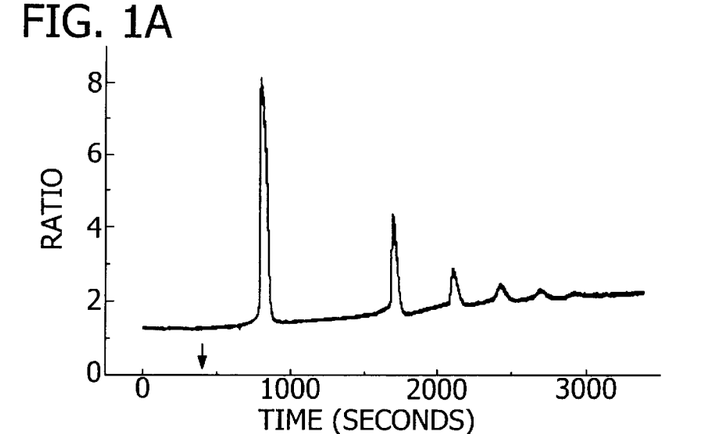
Figure 1B:
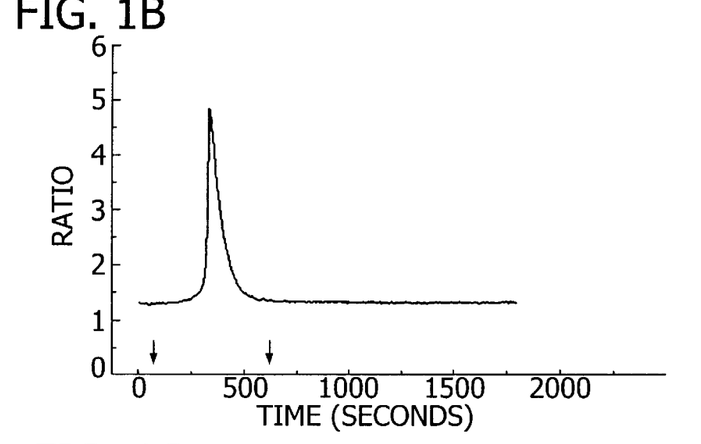

Incubation of porcine oocytes with thimerosal induced repetitive $Ca^{2+}$ transients in 56 of 56 oocytes. The oscillation started 324.9±23.8 sec after thimerosal administration, and the number of $Ca^{2+}$ spikes induced per oocyte was between 2 and 6 (mean±SE: 3.4±0.2). Characteristically, the first transient in each oocyte was of higher amplitude than the following ones. The oscillation generally stopped in 30–45 min. During this time, the $Ca^{2+}$ baseline drifted gradually upwards (FIG. 1A). DTT blocked the $Ca^{2+}$ transients induced by thimerosal: the addition of DTT (final concentration 8 mM) to the oocytes stopped the $Ca^{2+}$ oscillation in 9 out of 9 oocytes (FIG. 1B). DTT alone did not induce any changes in the $[Ca^{2+}]_i$ (data not shown).

Figure 1C:
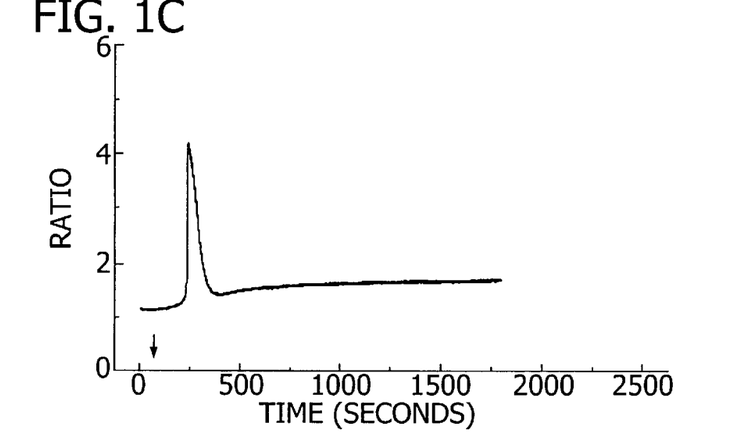
FIG. 1C: In $Ca^{2+}$-free medium, the number of additional transients was significantly lower. In this particular oocyte, there was no additional $Ca^{2+}$ release after the first transient induced by thimerosal (arrow).

In $Ca^{2+}$-free medium ($Ca^{2+}$-free HbT supplemented with 100 μM EGTA), thimerosal also induced a $Ca^{2+}$ transient with a similar amplitude (FIG. 1C). However, the number of additional spikes was reduced by the lack of external $Ca^{2+}$: in 60% of the oocytes (6/10), there was only one additional spike following the initial $Ca^{2+}$ transient. In the rest of the oocytes (4/10,) no other transients were induced.

In most cases, the $Ca^{2+}$ oscillation evoked by 200 μM thimerosal ceased about 30 min after the addition of thimerosal. Therefore, in the first set of experiments, porcine oocytes were incubated in the presence of the sulfhydryl oocyte-modifying reagent for 30 min, and the chromatin structure was evaluated. Nuclear staining revealed that the 30 minute thimerosal treatment itself did not induce complete activation of the oocytes, as 6 h after the stimulation, none of 124 oocytes formed pronuclei (Table 1). The 30 min incubation with thimerosal probably caused such severe damage to the spindles that no pronuclear formation occurred even after a 30 min culture in the presence of 8 mM DTT. Likewise, pronuclear formation was not observed after a shorter (10 min) exposure to thimerosal. However, a 10 min thimerosal stimulation followed by a 30 min incubation in the presence of 8 mM DTT resulted in a high rate of pronuclear formation (318/431: 73.8%). These oocytes completed second metaphase before entering interphase as evidenced by the fact that 76.3% of them extruded the second polar body. DTT alone could not stimulate pronuclear formation.

TABLE 1

Pronuclear Formation in Porcine Oocytes Following Treatment With Various Combinations of 200 µM Thimerosal and 8 mM DTT

| Treatment | No. of matured oocytes | No. (%) of oocytes having pronuclei |
|---|---|---|
| Thi. (30 min) | 124 | 0 (0)[a] |
| Thi. (30 min) + DTT (30 min) | 225 | 1 (0.4)[a] |
| Thi. (10 min) | 95 | 2 (2.1)[a] |
| Thi. (10 min) + DTT (30 min) | 431 | 318 (73.8)[b] |
| DTT (30 min) | 124 | 1 (0.8)[a] |

[a,b]Values having different superscript letters are significantly different ($p < 0.001$)

Figure 2A:
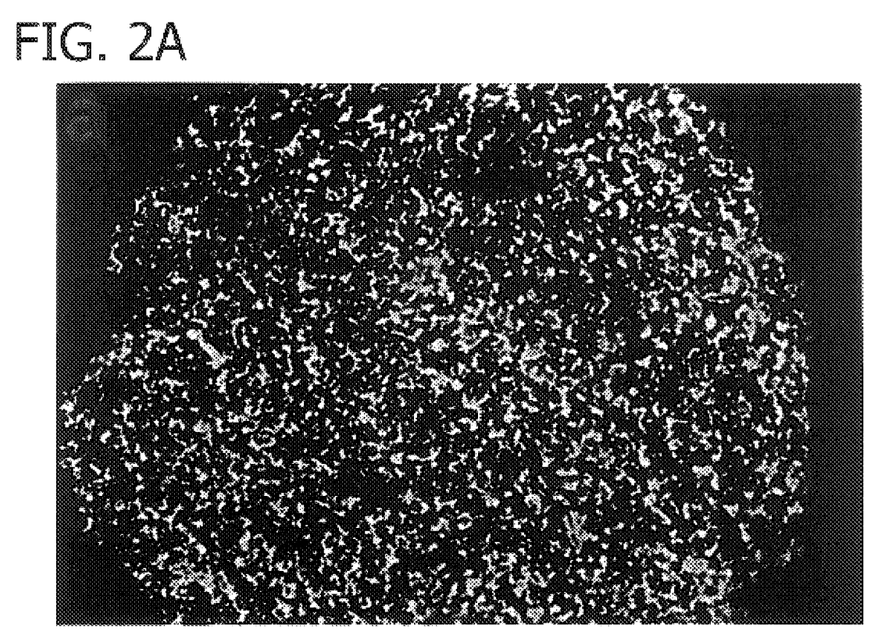
FIGS. 2a and 2b are micrographs showing the cortical granules in porcine oocytes. The number of cortical granules was significantly higher in the control (non-treated) oocyte (FIG. 2a) than in the oocyte treated with thimerosal/DTT (FIG. 2b). The bar indicates 20 µm.
Figure 2B:
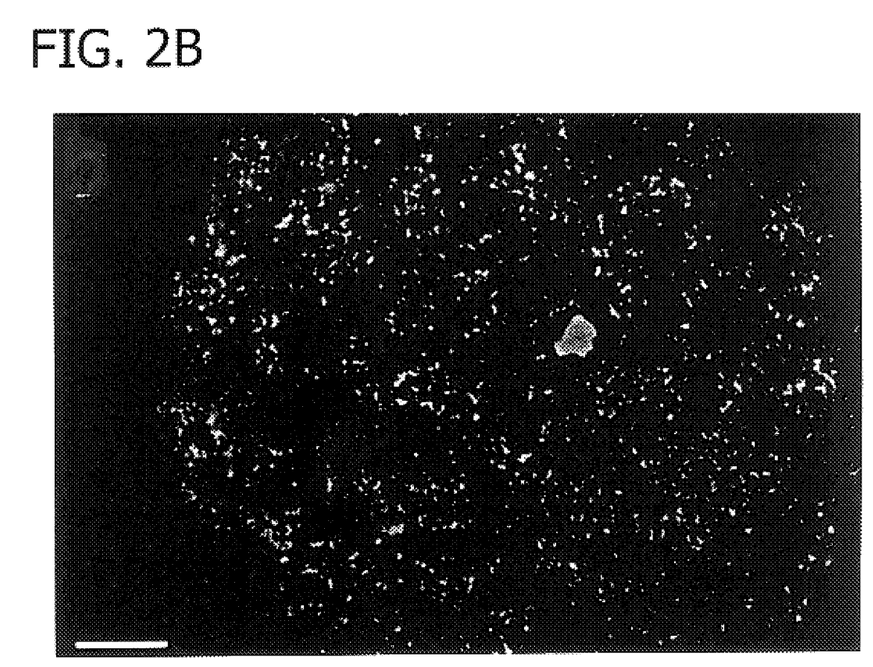

The mean number of cortical granules/100 $\mu m^2$ was 13.3±2.0 in the oocytes cultured with 200 µM thimerosal for 10 min followed by a 30 min incubation in the presence of 8 mM DTT (n=35). The control oocytes that were not exposed to thimerosal had significantly more cortical granules (51.0±2.3; n=26; p<0.001; FIG. 2). The cortical granule exocytosis also induced zona hardening. The mean time necessary to digest the zona pellucida of 50% of the oocytes was significantly longer in the thimerosal/DTT-treated groups than that in the non-treated groups (219.6±15.9 versus 152.0±15.9 sec; p=0.04; N=6)

When cultured in vitro, 42.0% (37/88) of the thimerosal (10 min)/DTT-treated (30 min) oocytes developed into compact morulae or blastocysts. Differential staining revealed that the blastocyst stage embryos had an average ICM nuclear number of 8.6±0.7, and TE nuclear number of 20.1±1.3. Following a 6 day culture in ligated oviducts, the percentage of thimerosal (10 min)/DTT-treated (30 min) oocytes that developed to the compact morula or blastocyst stage was 42.9% (61/142). The mean number of ICM and TE nuclei in these in vivo developed blastocysts were 12.5±1.0 and 63.6±9.2, respectively. Control oocytes that were exposed to DTT without prior thimerosal treatment did not develop to these stages either in vivo (0/86) or in vitro (0/161; p<0.001).

A published report of the foregoing results can be found in [29].

EXAMPLE 2

Effect of Thimerosal/DTT Treatment on Spindle Integrity

In this experiment, the effect of thimerosal/DTT treatment on spindle integrity in porcine oocytes was investigated.

The basic experimental procedures were as in Example 1. After treatment with various combinations of thimerosal and DTT, the oocytes were fixed in 3.7% paraformaldehyde for 2 h at 37° C. and permeabilized with 1% Triton X-100 in phosphate buffered saline (PBS) for 6 h at room temperature. They were then washed in PBS for 3 h before being transferred to blocking solution (2% BSA, 2% non-fat dry milk, 0.15 M glycine in PBS) for 1 h at room temperature. After another wash in PBS for 1 h, the microtubules were stained with FITC-conjugated anti α-tubulin antibody (Long et al. (1997) Theriogenology 47:309). The chromatin was stained with propidium iodide (Papaioannou et al. (1988) Development 102:793–803). The oocytes were then evaluated for spindle integrity using a laser scanning confocal microscope. The results are shown in Table 2.

TABLE 2

Spindle Integrity in Porcine Oocytes Following Treatment With Various Combinations of 200 µM Thimerosal and 8 mM DTT

| Treatment | Spindle Integrity |
|---|---|
| Thi. (30 min) | Spindle destroyed |
| Thi. (10 min) + DTT (30 min) | Spindle intact |
| Thi. (30 min) + DTT (60 min) | Spindle destroyed |
| DTT (120 min) | Spindle intact |
| Control (non-treated) | Spindle intact |

As shown in Table 2, treatment of porcine oocytes with thimerosal for 30 min destroyed the spindle. Treatment with thimerosal for 10 min followed by exposure to DTT for 30 min restored spindle integrity.

Treatment with thimerosal for a longer period, i.e., 30 min, followed by treatment with DTT for 60 min, did not reverse the effects of thimerosal. Under these conditions, spindle integrity was not restored, suggesting that there is an upper time limit beyond which the effects of thimerosal treatment on spindle integrity cannot be reversed by a reducing agent in oocytes. As expected, treatment with DTT alone yielded results similar to that obtained in the untreated control: the spindle remained intact.

These data demonstrate that the oocyte-modifying agent thimerosal destroys the meiotic spindle in unfertilized oocytes, and that treatment with a reducing agent such as DTT can reverse this damage if applied to the oocytes within a time period in which the effects of the oocyte-modifying agent remain reversible. In this case, the deleterious effects of thimerosal contact with oocytes for 30 min were not reversible by a subsequent 60 min treatment with DTT. Thus, the duration of contact of the oocyte-modifying agent with oocytes is a factor that affects activation of unfertilized mammalian oocytes exposed to a combination of an oocyte-modifying agent and a reducing agent.

EXAMPLE 3

Prevention of Polyspermy in Activated Oocytes

One of the events necessary for normal embryo development is fertilization of the oocyte by a single sperm cell. Current methods of in vitro fertilization in porcine oocytes suffer from a high incidence of fertilization by multiple sperm (reviewed by K. Niwa (1993) J. Reprod. Fertil. Suppl. 48:49–59). This is due to the inability of the fertilizing sperm to block additional sperm from the fertilization process. It is generally accepted that sperm blockage is accomplished by the release of cortical granules from the oocyte at the time of fertilization.

This experiment was performed to investigate the effect of oocyte activation on the prevention of polyspermy.

Oocyte maturation was performed as in Example 1. Also as in Example 1, oocytes were incubated with 200 µM thimerosal for 10 min, followed by a 30 min incubation with 8 mM DTT. In vitro fertilization of the treated oocytes was performed by washing cumulus-free oocytes three times with insemination medium (a modified Tris-buffered medium containing 113.1 mM NaCl, 3 mM KCl, 7.5 mM $CaCl_2 \cdot 2H_2O$, 5 mM Na-pyruvate, 11 mM glucose, 20 mM Tris (crystallized free base), 1 mM caffeine, and 0.1% BSA; Abeydeera et al. (1997) Biol. Reprod. 57:729–734). 30 to 35 oocytes were transferred into a 50 μl droplet of insemination medium covered with paraffin oil which had been equlibrated for 40 h at 39° C. in 5% $CO_2$ in air. The thimerosal-treated oocytes were washed six times in insemination medium for a total of 10 min, and then transferred to droplets of insemination medium. The dishes were kept in a $CO_2$ incubator until spermatozoa were added for insemination. For in vitro fertilization, one 0.2 ml frozen semen pellet, prepared according to Wang et al. (1991) *J. Reprod. Fertil.* 93:491–496, was thawed at 39° C. in 10 ml of PBS containing 1 mg/ml BSA and antibiotics. After being washed three times and collected by centrifugation at 1800×g for four min each time, spermatozoa were resuspended in insemination medium to produce a concentration of 1×10⁶ cells/ml. 50 μl of the sperm sample were added to the 50 μl fertilization drops containing the oocytes. Six hours after insemination, the oocytes were removed from the fertilization drops and assessed for sperm penetration and cortical granule exocytosis.

Cortical granule release was determined as in Example 1.

Sperm penetration was assessed by mounting the oocytes, fixation for 48–72 h in 25% (v/v) acetic acid in ethanol at room temperature, staining with 1% (w/v) orcein in 45% (v/v) acetic acid, and examination under a phase-contrast microscope at magnifications of 200× and 400×. Oocytes were considered penetrated when they had one or more swollen sperm heads and/or male pronuclei and their corresponding sperm tails.

In in vitro-matured pig oocytes, the thimerosal-induced calcium release triggered a rapid exocytosis of the cortical granules: two min after the calcium transient, 59.5% of the cortical granules were released (n=11). Five min after the calcium transient, 83.1% of the granules were released (n=11). This thimerosal-induced calcium transient triggered the release of the cortical granules that in turn prevented penetration by sperm. The percentage of penetrated oocytes after thimerosal treatment was only 1.5% (2/134). In comparison, approximately 50% of oocytes are penetrated by multiple sperm in normal in vitro fertilization.

EXAMPLE 4

Effect of Oocyte Maturation and Incubation Media on Oocyte Activation

This experiment was conducted in order to determine the effect of varying the medium in which the oocyte is matured and in which calcium transients are measured on the time to the first calcium transient after exposure to the oocyte-modifying agent.

In Example 1, oocytes were matured in vitro in NCSU-23 medium, and were exposed to thimerosal for 10 min to allow sufficient time for development of the first calcium transient, i.e., 324.9±23.8 sec after thimerosal addition, before reversal with DTT (note Table 1). The measurements were conducted in HbT medium.

In this experiment, calcium transients were measured in HbT or a modified Tris-buffered medium containing 113.1 mM NaCl, 3 mM KCl, 7.5 mM $CaCl_2.2H_2O$, 5 mM Na-pyruvate, 11 mM glucose, 20 mM Tris (crystallized free base), 1 mM caffeine, and 0.1% BSA (Abeydeera et al. (1997) *Biol. Reprod.* 57:729–734).

Oocyte maturation was carried out in vitro in NCSU-23 medium as in Example 1, in vitro in NCSU-37 medium, or in vivo as described below. The results are summarized in Table 3.

TABLE 3

Effect of Maturation and Incubation Media on Time From Thimerosal Addtion to First Calcium Transient in Porcine Oocytes

| Maturation System | Measurement Medium | Time to First $Ca^{+2}$ Transient |
| --- | --- | --- |
| In vitro-NCSU23 | HbT | 324 ± 23[a] sec (n = 56) |
| In vitro-NSCU23 | Tris-buffered medium | 510 ± 62[b] sec (n = 8) |
| In vitro-NCSU37 | HbT | 667 ± 47[c] sec (n = 14) |
| In vivo | HbT | 431 ± 47[ab] sec (n = 14) |
| In vivo | Tris buffered medium | 501 ± 50[b] sec (n = 12) |

[abc]$p < 0.05$

As shown in Table 3, in the Tris-buffered medium the time to the first calcium transient after addition of thimerosal was 510±62 sec. When thimerosal was added to in vivo-matured oocytes collected 48 h after the onset of oestrus (Prather et al. (1991) *Theriogenology* 35:1147–1151), the response time to the first calcium transient increased to 431±47 sec. The response time to the first calcium transient in in vivo-matured oocytes suspended in the Tris-buffered medium described above was 501±50 sec. When the in vitro maturation system was changed to NCSU-37 medium (Petters et al. (1993) *J. Reprod. Fertil. Suppl.* 48:61–73) and measurement of calcium transients was conducted in HbT medium, the time to the first transient was 667±47 sec.

These data demonstrate that the time of oocyte exposure to the oocyte-modifying agent necessary to observe the first calcium transient can be influenced by the manner (in vivo vs. in vitro) and medium in which the oocyte is matured, as well as the medium used during oocyte treatment with the oocyte-modifying agent and the medium in which the calcium transients measurements are made. Generally speaking, the time of oocyte exposure to an oocyte-modifying agent, such as thimerosal, should be a period of time effective to activate an oocyte when followed by exposure to a reducing agent. Concomitantly, the time of oocyte exposure to a reducing agent, such as DTT, should be a period of time effective to activate an oocyte when preceded by exposure to an oocyte-modifying agent. Such periods can be determined by the routine assay methods outlined herein. In the case of the particular maturation systems and measuring media described herein, summarized in Table 3, the effective time of exposure of oocytes to an oocyte-modifying agent can be in the range of from about 5 min to about 15 min, more preferably from about 5 min to about 12 min. The effective time of subsequent exposure of oocytes to a reducing agent can generally be in the range of from about 5 minutes to about 1 hour, preferably from about 10 minutes to about 45 minutes, more preferably from about 20 minutes to about 40 minutes, most preferably about 30 minutes.

EXAMPLE 5

Effect of Thimerosal on Time to the First Calcium Transient in Bovine Oocytes

The time to the first calcium transient in the presence of thimerosal was also determined in in vitro-matured bovine oocytes.

Bovine oocytes were obtained from Bomed, Inc., Madison, Wis. 53705. Oocytes were taken from antral follicles and selected for use if having a compact cumulus several cell layers thick. Oocytes were processed in TC199 with Earle's salts (Gibco BRL, Gaithersburg, Md.) supplemented with HEPES buffer, 0.22 mM sodium pyruvate, 25 μg/ml gentamicin, and 3 mg/ml bovine serum albumin. The maturation medium was TC199 with Earle's salts supplemented with bovine LH and FSH from Sioux Biochemicals (Sioux Center, IA 51250), 0.22 mM sodium pyruvate, 25 μg/ml gentamicin, and 10% fetal calf serum added. Oocytes were shipped at 39° C. at the germinal vesicle stage in 2 ml vials filled with maturation medium equilibrated in 5% $CO_2$ in air at 39° C. and high humidity.

Measurement of the time to the first calcium transient in the presence of thimerosal was performed as in Example 1. Under these conditions, the time to the first calcium transient was 294±26.8 sec (n=10); additional transients were blocked by DTT.

Discussion

The results presented herein demonstrate that, as in oocytes of other species studied, thimerosal evoked sustained oscillation in the $[Ca^{2+}]_i$ in mature porcine and bovine oocytes. Elevated $[Ca^{2+}]_i$ was also detected in the absence of external $Ca^{2+}$, clearly indicating that the $Ca^{2+}$ transients induced by thimerosal were the result of $Ca^{2+}$ release from the intracellular stores. However, oscillation following the initial transient required external $Ca^{2+}$, as in its absence the number of additional spikes decreased remarkably. This is consistent with the data in bovine oocytes [8], which showed at most one additional transient in $Ca^{2+}$-free medium. Interestingly, in mouse oocytes, $Ca^{2+}$ in the external medium was not a prerequisite for $Ca^{2+}$ injection-induced repetitive hyperpolarizing membrane responses [3] or repetitive $Ca^{2+}$ transients [6]. The reason for this difference in the necessity of external $Ca^{2+}$ to sustain the thimerosal-induced $Ca^{2+}$ oscillation is not clear.

The sulfhydryl reducing agent DTT could totally block the $Ca^{2+}$ release triggered by thimerosal. This is consistent with the hypothesis that thimerosal acts by oxidation of critical sulfhydryl groups on either the $InsP_3$ [19] or the ryanodine [2] receptor.

The mechanism by which thimerosal induces $Ca^{2+}$ release is not known in detail. It has been shown previously that sulfhydryl oxidation triggers rapid $Ca^{2+}$ release from terminal cisternae of the sarcoplasmic reticulum in skeletal muscle, and that reduction of the disulfide formed causes the $Ca^{2+}$ release pathway to close [20, 21]. Also in skeletal muscle, sulfhydryl regeants interact with $Ca^{2+}$ release protein, the ryanodine receptor [22]. The sulfhydryl reagent thimerosal was then reported to induce $[Ca^{2+}]_i$ increases in platelets and leucocytes [23, 24]. A model was suggested in which reversible oxidation and reduction of critical sulfhydryl groups on the $Ca^{2+}$ release protein results in the opening and closing of the $Ca^{2+}$ release channel [25]. Whether or not these sulfhydryl groups are directly involved in the triggering of the $Ca^{2+}$ transients at fertilization is not known. The mechanism might be different because DTT was shown to reverse the effect of thimerosal, but it enhanced that of the fertilizing spermatozoa [5].

At fertilization, the elevated $[Ca^{2+}]_i$ triggers the release of the cortical granules, which in turn causes the zona reaction to prevent polyspermy. The $Ca^{2+}$ transients triggered by thimerosal also induced cortical granule exocytosis and subsequent zona hardening. On the average, 73.9% of the cortical granules were released after treatment with thimerosal. This rate of release is similar to that induced by the fertilizing spermatozoa: in porcine oocytes matured in vitro, the number of cortical granules was found to decrease from 56.9±19.8 to 6.4±4.4 (88.7%) after sperm penetration [26]. These results are consistent with those obtained in mouse oocytes [5], where the same responses were observed after $Ca^{2+}$ oscillation induced by 100 μM thimerosal.

The changes that thimerosal induces in oocytes are very similar to those induced by sperm at fertilization. But despite of all these changes, thimerosal arrests oocytes in metaphase, thus preventing completion of meiosis and progression into interphase. Immunocyto-chemical examination of tubulin and chromatin revealed that exposure of the oocytes to thimerosal completely destroyed the spindle [5]. Since an intact spindle is required for transition from M-phase to interphase [27], it had been concluded that thimerosal could not stimulate pronuclear formation.

Nonetheless, DTT was reported to reduce the oxidized tubulin sulfhydryl groups: after DTT incubation, more than 70% of mouse occytes regenerated the metaphase spindles previously deteriorated by thimerosal [5]. In the experiments described herein, exposure of metaphase II oocytes to thimerosal for 30 min caused changes in the spindles which could not be regenerated by DTT. However, DTT was able to restore the damage to the spindles caused by a 10 min thimerosal treatment, so that functional spindles were present during the subsequent series of mitotic divisions. The $Ca^{2+}$ measurements in Example 1 indicated that only one $Ca^{2+}$ transient was evoked during the first 10 min of thimerosal incubation. Apparently, this single $Ca^{2+}$ transient provided sufficient stimulus to support development, since a high percentage of blastocysts with well developed ICM and TE was formed after a 6 day culture either in vitro or in vivo.

The present results are consistent with the finding that the sulfhydryl reagent thimerosal induces repetitive $Ca^{2+}$ spikes in oocytes by modifying critical sulfhydryl groups on intracellular $Ca^{2+}$ release proteins. Thimerosal also modifies the tubulin sulfhydryl groups, causing disassembly of the meiotic spindle. However, this later effect can be reversed by the reducing agent DTT, so that the combined thimerosal/DTT treatment induces full activation of oocytes that supports development to the compact morula or blastocyst stage.

The invention being thus described, it will be obvious that the same can be varied in many ways. Such variations are not to be regarded as a departure from the spirit and scope of the present invention, and all such modifications and equivalents as would be obvious to one skilled in the art are intended to be included within the scope of the following claims.

Literature Cited

1. Miyazaki S. et al., Dev Biol 1993; 158:62–78.
2. Swann K., Biochem J 1992; 287:79–84.
3. Swann K., FEBS Lett 1991; 278:175–178.
4. Miyazaki S. et al., FEBS Lett 1992; 309:180–184.
5. Cheek T. R. et al., Development 1993; 119:179–189.
6. Kline J. T. et al., Biol Reprod 1994; 50:193–203.
7. Fissore R. A et al., Dev Biol 1993; 159:122–130.
8. Fissore R. A. et al., Biol Reprod 1995; 53:766–774.
9. Homa S. T. et al., Hum Reprod 1994; 9:2356–2361.
10. Herbert M. et al., Hum Reprod 1995; 10:2183–2186.
11. Kuriyama R, et al., J Biochem 1974; 76:651–654.
12. Abeydeera L R, et al., Theriogenology 1997; 47:313.
13. Bavister B D, et al., Biol Reprod 1983; 28:235–247.
14. Macháty Z, et al., Biol Reprod 1997; 56:921–930.

15. Yoshida M, et al., Mol Reprod Dev 1993; 36:462–468.
16. Wang W H, et al., Biol Reprod 1997; in press.
17. Prather R S, et al., Mol Reprod Dev 1996; 45:38–42.
18. Wilkinson L., SYSTAT, Inc.; 1990.
19. Miyazaki S et al., FEBS Lett 1992; 309:180–184.
20. Trimm J L, et al., J Biol Chem 1986; 261:16092–16098.
21. Abramson J J, et al., Arch Biochem Biophys 1988; 263:245–255.
22. Pessah I N, et al., Mol Pharmacol 1987; 31:232–238.
23. Hecker M, et al., Biochem Biophys Res Commun 1989; 159:961–968.
24. Hatzelmann A, et al., Biochem Pharmacol 1990; 39:559–567.
25. Abramson J J, et al., J Bioenerg Biomemb 1989; 21:283–294.
26. Wang W H, et al., Mol Reprod Dev 1997; (submitted)
27. Maro B et al., J Embryol Exp Morph 1986; 92:11–32.
28. Prather R S, Proc Soc Exp Biol Med 1996; 212:38–43.
29. Machaty Z et al., Biology of Reproduction 1997; 57:1123–1127.

What is claimed is:

1. A method of activating an unfertilized mammalian oocyte, comprising contacting said unfertilized mammalian oocyte with an oocyte-modifying agent followed by a reducing agent,
   wherein said mammalian oocyte is incubated with said oocyte-modifying agent and said reducing agent, respectively, for a time and under conditions such that said unfertilized mammalian oocyte is activated, and
   culturing said activated mammalian oocyte to at least the pronuclear stage.

2. The method of claim 1, wherein said oocyte-modifying agent is selected from the group consisting of thimerosal; t-butyl hydroperoxide; thiourea; phenylephrine; an N-aklylmaleimide; oxidized glutathione; an α-haloacid; iodoacetamide; p-mercuribenzoate; p-chloromercuribenzoate; 5,5'-dithiobis(2-nitrobenzoic acid); (2-trimethylammonium)ethylmethanethiosulfonate; and (2-sulfonatoethyl)methanethiosulfonate.

3. The method of claim 1, wherein said reducing agent is selected from the group consisting of dithiothreitol, dithioerythritol; β-mercaptoethanol; cysteine; reduced glutathione; reduced thiourea; thioglycolate; and ascorbic acid.

4. The method of claim 1, wherein the concentration of said oocyte-modifying agent is in the range of from about 1 nm to about 1 mM, and the concentration of said reducing agent is in the range of from about 0.1 mM to about 250 mM.

5. The method of claim 1, wherein said time during which said unfertilized mammalian oocyte is incubating with said oocyte-modifying agent is in the range of from about 5 minutes to about 20 minutes.

6. The method of claim 5, wherein said time during which said unfertilized mammalian oocyte is incubating with said oocyte-modifying agent is in the range of from about 10 minutes to about 12 minutes.

7. The method of claim 6, wherein said time during which said unfertilized mammalian oocyte is incubating with said oocyte-modifying agent is about 10 minutes.

8. The method of claim 1, wherein said time during which said unfertilized mammalian oocyte is incubating with said reducing agent is in the range of from about 5 minutes to about 1 hour.

9. The method of claim 8, wherein said time during which said unfertilized mammalian oocyte is incubating with said reducing agent is in the range of from about 20 minutes to about 40 minutes.

10. The method of claim 9, wherein said time during which said unfertilized mammalian oocyte is incubating with said oocyte-modifying agent is about 30 minutes.

11. The method of claim 1, wherein said incubating said unfertilized mammalian oocyte with an oocyte-modifying agent followed by a reducing agent comprises a time interval in the range of from about 5 seconds to 5 about 5 minutes between exposure of said unfertilized mammalian oocyte to said oocyte-modifying agent and said reducing agent.

12. The method of claim 1, wherein said unfertilized mammalian oocyte is selected from the group consisting of an unfertilized porcine oocyte, an unfertilized bovine oocyte, an unfertilized mouse oocyte, an unfertilized sheep oocyte, an unfertilized goat oocyte, an unfertilized horse oocyte, an unfertilized cat oocyte, an unfertilized dog oocyte, and an unfertilized human oocyte.

13. The method of claim 1, wherein activation of said unfertilized mammalian oocyte initiates development of said oocyte such that it develops anywhere from the 2-, 4-, or 8-cell stage to the blastocyst stage when cultured in vitro or in vivo.

14. A method of activating an unfertilized mammalian oocyte, comprising contacting said unfertilized mammalian oocyte with thimerosal for about 10 minutes, followed by incubating said unfertilized mammalian oocyte with dithiotreitol for about 30 minutes, and then culturing said unfertilized mammalian oocyte to at least the pronuclear stage.

15. A method for transplanting a nucleus from a mammalian cell to a recipient mammalian oocyte, comprising:
   (a) isolating the membrane-bounded nucleus from said mammalian cell;
   (b) removing the nuclear chromosomal material from said recipient mammalian oocyte, thereby preparing an enucleated recipient mammalian oocyte;
   (c) introducing said membrane-bounded nucleus from said mammalian cell into said enucleated recipient mammalian oocyte to form an oocyte containing said nucleus from said mammalian cell;
   (d) reprogramming the developmental cascade of events of said nucleus from said mammalian cell;
   (e) incubating said oocyte containing said nucleus from said mammalian cell of step (d) with an oocyte-modifying agent followed by a reducing agent, wherein said oocyte is incubating with said oocyte-modifying agent and said reducing agent, respectively, for a time and under conditions such that said oocyte is activated; and
   (f) culturing said activated oocyte of step (e) in vitro or in vivo.

16. A method for transplanting a nucleus from a mammalian embryo to a recipient mammalian oocyte, comprising:
   (a) isolating the membrane-bounded nucleus from a cell of said mammalian embryo;
   (b) removing the nuclear chromosomal material from said recipient mammalian oocyte, thereby preparing an enucleated recipient mammalian oocyte;
   (c) introducing said membrane-bounded nucleus from said cell of said mammalian embryo into said enucleated recipient mammalian oocyte to form an oocyte containing said nucleus from said cell of said mammalian embryo;
   (d) reprogramming the developmental cascade of events of said nucleus from said cell of said mammalian embryo;
   (e) incubating said oocyte containing said nucleus from said cell of said mammalian embryo of step (d) with an oocyte-modifying agent followed by a reducing agent, wherein said oocyte is incubating with said oocyte-modifying agent and said reducing agent, respectively, for a time and under conditions such that said oocyte is activated; and (f) culturing said activated oocyte of step (e) in vitro or in vivo.

17. A method for transplanting a nucleus from a mammalian fetus to a recipient mammalian oocyte, comprising:

(a) isolating the membrane-bounded nucleus from a cell of said mammalian fetus;

(b) removing the nuclear chromosomal material from said recipient mammalian oocyte, thereby preparing an enucleated recipient mammalian oocyte;

(c) introducing said membrane-bounded nucleus from said cell of said mammalian fetus into said enucleated recipient mammalian oocyte to form an oocyte containing said nucleus from said cell of said mammalian fetus;

(d) reprogramming the developmental cascade of events of said nucleus from said cell of said mammalian fetus;

(e) incubating said oocyte containing said nucleus from said cell of said mammalian fetus of step (d) with an oocyte-modifying agent followed by a reducing agent, wherein said oocyte is incubating with said oocyte-modifying agent and said reducing agent, respectively, for a time and under conditions such that said oocyte is activated; and (f) culturing said activated oocyte of step (e) in vitro or in vivo.

18. A method for transplanting a nucleus from an adult mammal to a recipient mammalian oocyte, comprising:

(a) isolating the membrane-bounded nucleus from a cell of said adult mammal;

(b) removing the nuclear chromosomal material from said recipient mammalian oocyte, thereby preparing an enucleated recipient mammalian oocyte;

(c) introducing said membrane-bounded nucleus from said cell of said adult mammal into said enucleated recipient mammalian oocyte to form an oocyte containing said nucleus from said cell of said adult mammal;

(d) reprogramming the developmental cascade of events of said nucleus from said cell of said adult mammal;

(e) incubating said oocyte containing said nucleus from said cell of said adult mammal of step (d) with an oocyte-modifying agent followed by a reducing agent, wherein said oocyte is incubating with said oocyte-modifying agent and said reducing agent, respectively, for a time and under conditions such that said oocyte is activated; and (f) culturing said activated oocyte of step (e) in vitro or in vivo.

19. A method for producing a cloned mammalian embryo, comprising:

(a) isolating a membrane-bounded nucleus from a cell of said mammalian embryo;

(b) removing the nuclear chromosomal material from a recipient mammalian oocyte, thereby preparing an enucleated recipient mammalian oocyte;

(c) introducing said membrane-bounded nucleus from said cell of said mammalian embryo into said enucleated recipient mammalian oocyte to form an oocyte containing said nucleus from said cell of said mammalian embryo;

(d) reprogramming the developmental cascade of events of said nucleus from said cell of said mammalian embryo;

(e) incubating said oocyte containing within its cytoplasm said nucleus from said cell of said mammalian embryo of step (d) with an oocyte-modifying agent followed by a reducing agent, wherein said oocyte is incubating with said oocyte-modifying agent and said reducing agent, respectively, for a time and under conditions such that said oocyte is activated; and (f) culturing said activated oocyte of step (e) in vivo or in vitro to produce a cloned mammalian embryo.

20. A method for producing a cloned mammal, comprising:

(a) isolating a membrane-bounded nucleus from a cell of said mammal;

(b) removing the nuclear chromosomal material from an unfertilized recipient mammalian oocyte, thereby preparing an enucleated recipient mammalian oocyte;

(c) introducing said membrane-bounded nucleus from said cell of said mammal into said enucleated recipient mammalian oocyte to form an oocyte containing said nucleus from said cell of said mammal;

(d) reprogramming the developmental cascade of events of said nucleus from said cell of said mammal;

(e) incubating said oocyte containing within its cytoplasm said nucleus of said cell from said mammal with an oocyte-modifying agent followed by a reducing agent, wherein said oocyte is incubating with said oocyte-modifying agent and said reducing agent, respectively, for a time and under conditions such that said oocyte is activated;

(f) culturing said activated oocyte of step (e) in vitro or in vivo; and (g) transferring said cultured, activated oocyte of step (f) to the oviduct or uterus of a recipient maternal mammal to produce a cloned mammal.

21. A method of studying genetic imprinting in a mammal, comprising:

(a) incubating an unfertilized mammalian oocyte with an oocyte-modifying agent followed by a reducing agent, wherein said unfertilized mammalian oocyte is incubating with said oocyte-modifying agent and said reducing agent, respectively, for a time and under conditions such that said unfertilized mammalian oocyte is activated; and (b) determining whether a gene of interest is expressed or not during culturing of said activated mammalian oocyte.

* * * * *

UNITED STATES PATENT AND TRADEMARK OFFICE
CERTIFICATE OF CORRECTION

PATENT NO. : 6,211,429 B1
DATED : April 3, 2001
INVENTOR(S) : Zoltan Machaty et al.

Page 1 of 1

It is certified that error appears in the above-identified patent and that said Letters Patent is hereby corrected as shown below:

Column 21,
Line 47, claim 5, "incubating" should read -- incubated --.
Line 51, claim 6, "incubating" should read -- incubated --.
Line 54, claim 7, "incubating" should read -- incubated --.
Line 58, claim 8, "incubating" should read -- incubated --.
Line 62, claim 9, "incubating" should read -- incubated --.
Line 66, claim 10, "incubating" should read -- incubated --.

Column 22,
Line 4, claim 11, "5 seconds to 5 about 5 minutes" should read -- 5 seconds to about 5 minutes --.
Line 43, claim 15, "incubating" should read -- incubated --.

Column 23,
Line 2, claim 16, "incubating" should read -- incubated --.
Line 26, claim 17, "incubating" should read -- incubated --.
Line 50, claim 18, "incubating" should read -- incubated --.

Column 24,
Line 15, claim 19, "incubating" should read -- incubated --.
Line 37, claim 20, "incubating" should read -- incubated --.
Line 51, claim 21, "incubating" should read -- incubated --.

Signed and Sealed this

Eleventh Day of December, 2001

Attest:

*Nicholas P. Godici*

*Attesting Officer*

NICHOLAS P. GODICI
*Acting Director of the United States Patent and Trademark Office*